United States Patent
Bachmann

(10) Patent No.: US 12,187,979 B2
(45) Date of Patent: Jan. 7, 2025

(54) 1-(BICYCLO[2.2.1]HEPT-5-EN-2-YL)ETHAN-1-ONE O-METHYLOXIME AS A FRAGRANCE ADDITIVE

(71) Applicant: GIVAUDAN SA, Vernier (CH)

(72) Inventor: Jean-Pierre Bachmann, Waedenswil (CH)

(73) Assignee: Givaudan SA, Vernier (CH)

( * ) Notice: Subject to any disclaimer, the term of this patent is extended or adjusted under 35 U.S.C. 154(b) by 528 days.

(21) Appl. No.: 17/605,709

(22) PCT Filed: May 13, 2020

(86) PCT No.: PCT/EP2020/063265
§ 371 (c)(1),
(2) Date: Oct. 22, 2021

(87) PCT Pub. No.: WO2020/234069
PCT Pub. Date: Nov. 26, 2020

(65) Prior Publication Data
US 2022/0145213 A1   May 12, 2022

(30) Foreign Application Priority Data

May 17, 2019   (GB) ..................................... 1906953

(51) Int. Cl.
| | | |
|---|---|---|
| *C11D 3/50* | (2006.01) | |
| *A61K 8/40* | (2006.01) | |
| *A61Q 5/02* | (2006.01) | |
| *C07C 251/42* | (2006.01) | |
| *C11B 9/00* | (2006.01) | |

(52) U.S. Cl.
CPC .............. *C11B 9/0046* (2013.01); *A61K 8/40* (2013.01); *A61Q 5/02* (2013.01); *C07C 251/42* (2013.01); *C07C 2602/42* (2017.05)

(58) Field of Classification Search
CPC ....... C11D 3/0068; C11D 3/3917; C11D 3/50; C11D 3/502; C11D 3/505; C11D 7/3209; C11D 9/225; C11D 9/44; C11D 9/442; C11D 9/17–06; C11D 2111/12
See application file for complete search history.

(56) References Cited

U.S. PATENT DOCUMENTS

| | | | |
|---|---|---|---|
| 2004/0043916 A1* | 3/2004 | Narula .................. | C11B 9/0061 568/660 |
| 2004/0043917 A1* | 3/2004 | Narula .................. | C07D 317/58 568/660 |
| 2015/0299614 A1* | 10/2015 | Flachsmann .......... | C11B 9/0061 564/256 |

FOREIGN PATENT DOCUMENTS

| | | |
|---|---|---|
| EP | 0071248 A1 | 2/1983 |
| EP | 0672746 A1 | 9/1995 |
| EP | 0980863 A | 2/2000 |
| WO | 2019076926 A1 | 4/2019 |

OTHER PUBLICATIONS

International Search Report and Written Opinion of the International Searching Authority for corresponding application PCT/EP2020/063265 dated Aug. 3, 2020.
Anonymous; Database Registry [Online] Chemical Abstracts Service, Columbus, Ohio, US; Database accession No. 1865872-71-4.
Anonymous; Aurora Building Blocks Cat. Feb. 2019, Database accession No. 0335676374.
Anonymous; UORSY Building Blocks Lib. Cat. Jan. 2019, Database accession No. 1388434336.
Shanker, R. et al., "Oxazaborolidinone-Catalyzed Enantioselective Diels□-Alder Reaction of Acyclic a,b-, Unsaturated Ketones", J. Org. Chem. 2008, 73, 212-218.

* cited by examiner

*Primary Examiner* — Charles I Boyer
(74) *Attorney, Agent, or Firm* — Norris McLaughlin, PA

(57) ABSTRACT

The disclosure relates to an oximether possessing powerful green fruity anisic banana olfactory properties. The invention furthermore refers to a method of its production, and to fragrance compositions comprising it.

12 Claims, No Drawings

1-(BICYCLO[2.2.1]HEPT-5-EN-2-YL)ETHAN-1-ONE O-METHYLOXIME AS A FRAGRANCE ADDITIVE

This is an application filed under 35 USC 371 based on PCT/EP2020/063265 (WO 2020/234069), filed 13 May 2020, which claimed priority to GB 1906953.3 filed 17 May 2019. The present application claims the full priority benefit of all prior applications and incorporates by reference their full disclosures as if set forth herein.

The present invention relates to 1-(bicyclo[2.2.1]hept-5-en-2-yl)ethan-1-one O-methyl oxime possessing powerful green fruity anisic banana olfactory properties. The invention furthermore refers to a method of its production, and to fragrance compositions comprising it.

In the fragrance and flavor industry, perfumers and flavorists are continually looking for new compounds of high impact odors, or imparting new odor notes.

Compounds possessing powerful fruity green odor profiles are very attractive as widely suitable odor notes, especially for the use in fabric and personal care products.

Oxime ethers and their use as fragrance ingredients are generally known in the art. A long list of oxime ethers are disclosed in EP 0 672 746, possessing a very natural green and fruity odor notes. Two bicyclic compounds have been disclosed. 5-Methyl-8-isopropyl-bicyclo[2.2.2]oct-5-en-2-carbaldehyde O-methyl oxime possessing a woody, green odor profile, and 1,5-dimethyl-bicyclo[3.2.1]octan-8-on O-methyl oxime possessing a camphoraceous, eucalyptus odor profile, both of which do not belong to the preferred group of compounds.

Surprisingly it was found that 1-(bicyclo[2.2.1]hept-5-en-2-yl)ethan-1-one O-methyl oxime not only possess a very powerful fruity green odor profile but also is a highly blooming fragrance ingredient.

A fragrance "bloom" refers to the short term impact of an ingredient at a certain distance from the fragrance source. Short term means a few seconds to a few minutes after an external action has been applied to the fragrance ingredient itself. Such an action (or event) can be multiple in nature. Opening a fragrance flask, spraying a fragrance solution in the air or on the skin, contacting a perfumed product with a surface or with water, and in particular diluting a perfumed product with water, are typical actions capable of inducing a bloom. Both, perfumes and individual fragrance ingredients, can be classified in low blooming to high blooming perfume/fragrance ingredient, whereas a high bloom is highly desired by consumers in the today market place.

Although "bloom" is typically a time-dependent dynamic performance attribute of a fragrance it is measured after a certain time, but not later than 30 minutes, preferably 15 to 20 minutes, after the action has taken place. Typically, the assessment is performed in a closed volume of air, for example in a non-ventilated booth. Typically a panelist performs the assessment by smelling a certain volume of air (e.g. one or two breaths) in the booth through a small window which is open only during the assessment. Typically, the window is located between 0.5 meter and 2 meters apart from the source, preferably between 0.8 meter and 1.5 meter, for example 1.3 meter.

The exact geometry of the experimental set-up is not critical, but it must be reproducible from one assessment to the other.

All the attributes mentioned above, taken together, make 1-(bicyclo[2.2.1]hept-5-en-2-yl)ethan-1-one O-methyl oxime highly desirable for the fragrance industry. Whereas a CAS number has been allocated to the chemical structure of 1-(bicyclo[2.2.1]hept-5-en-2-yl)ethan-1-one O-methyl oxime, no publication defining it is available.

In a first aspect there is provided the use of 1-(bicyclo[2.2.1]hept-5-en-2-yl)ethan-1-one O-methyl oxime as fragrance. The skilled person will appreciate that 1-(bicyclo[2.2.1]hept-5-en-2-yl)ethan-1-one O-methyl oxime consists of E and Z isomers at the C=N double bond of the oxime ether. Furthermore, 1-(bicyclo[2.2.1]hept-5-en-2-yl)ethan-1-one O-methyl oxime, comprises three chiral centers and as such exist as a mixture of endo/exo isomers. For the sake of clarity, this includes the following racemic stereoisomers: rel-(E)-1-((1R,2S,4R)-bicyclo[2.2.1]hept-5-en-2-yl)ethan-1-one O-methyl oxime, rel-(E)-1-((1R,2R,4R)-bicyclo[2.2.1]hept-5-en-2-yl)ethan-1-one O-methyl oxime, rel-(Z)-1-((1R,2S,4R)-bicyclo[2.2.1]hept-5-en-2-yl)ethan-1-one O-methyl oxime, rel-(Z)-1-((1R,2R,4R)-bicyclo[2.2.1]hept-5-en-2-yl)ethan-1-one O-methyl oxime.

Resolving stereoisomers adds to the complexity of manufacture and purification of 1-(bicyclo[2.2.1]hept-5-en-2-yl)ethan-1-one O-methyl oxime and so it is preferred to use it as a mixture of their stereoisomers simply for economic reasons. However, if it is desired to prepare individual stereoisomers, this may be achieved according to methods known in the art, e.g. preparative HPLC and GC, crystallization or stereoselective synthesis.

In a further aspect there is provided a fragrance composition or perfumed product comprising 1-(bicyclo[2.2.1]hept-5-en-2-yl)ethan-1-one O-methyl oxime. The compound may be added directly to the product or may admixed with other, known fragrance ingredients resulting in a fragrance composition, and then added to the product.

The following list comprises examples of known fragrance ingredients, which may be combined with 1-(bicyclo[2.2.1]hept-5-en-2-yl)ethan-1-one O-methyl oxime:

essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;

alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;

aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl)ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)

ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;

ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);

esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);

macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and heterocycles, e.g. isobutylquinoline (2-isobutylquinoline).

In a specific embodiment the fragrance composition comprising 1-(bicyclo[2.2.1]hept-5-en-2-yl)ethan-1-one O-methyl oxime, may further comprise one or more pro-perfumes, including 1-butoxy-3-((1E,4Z)-hepta-1,4-dien-1-yl)benzene, (4-(dodecylthio)-4-methylpentan-2-one, 2-ethoxy-4-((1E,4Z)-hepta-1,4-dien-1-yl)phenol, and ethyl 2-acetyl-4-methyltridec-2-enoate.

As used herein, "fragrance composition" means any composition comprising 1-(bicyclo[2.2.1]hept-5-en-2-yl)ethan-1-one O-methyl oxime and a base material, e.g. a diluent conventionally used in conjunction with fragrance ingredients, such as diethyl phthalate (DEP), dipropylene glycol (DPG), isopropyl myristate (IPM), triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

1-(Bicyclo[2.2.1]hept-5-en-2-yl)ethan-1-one O-methyl oxime may be used in a broad range of perfumed products, e.g. in any field of fine and functional perfumery, such as perfumes, air care products, household products, laundry products, body care products and cosmetics. The compound can be employed in widely varying amounts, depending upon the specific application and on the nature and quantity of other fragrance ingredients. The proportion is typically from 0.001 to 30 (including, e.g., 5, 10, 15, 20, 25) weight percent of the application. In one embodiment, compounds of the present invention may be employed in perfumed products like a fabric softener in an amount of from 0.001 to 1 weight % (e.g. 0.01-0.3 weight percent). In another embodiment, compounds of the present invention may be used in detergent products (including powder detergent) in amounts from 0.1 to 10 weight present. In a further embodiment, compounds of the present invention may be used in fine perfumery in amounts from 0.1 to 30 weight percent (e.g. up to about 20 weight percent), more preferably between 0.5 and 15 weight percent. However, these values are given only by way of example, since the experienced perfumer may also achieve effects or may create novel accords with lower or higher concentrations.

1-(Bicyclo[2.2.1]hept-5-en-2-yl)ethan-1-one O-methyl oxime may be employed in a consumer product base simply by directly mixing 1-(bicyclo[2.2.1]hept-5-en-2-yl)ethan-1-one O-methyl oxime, or a fragrance composition comprising 1-(bicyclo[2.2.1]hept-5-en-2-yl)ethan-1-one O-methyl oxime with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof.

Thus, there is provided in a further aspect a method of manufacturing a perfumed product, comprising the incorporation of 1-(bicyclo[2.2.1]hept-5-en-2-yl)ethan-1-one O-methyl oxime, as a fragrance ingredient, either by directly admixing the compound to the consumer product base or by admixing a fragrance composition comprising 1-(bicyclo[2.2.1]hept-5-en-2-yl)ethan-1-one O-methyl oxime, which may then be mixed with a consumer product base, using conventional techniques and methods. Through the addition of an olfactory acceptable amount of 1-(bicyclo[2.2.1]hept-5-en-2-yl)ethan-1-one O-methyl oxime the odor notes of a consumer product base will be improved, enhanced, or modified.

Thus, the invention furthermore provides a method for improving, enhancing or modifying a consumer product base by means of the addition thereto of an olfactorily acceptable amount of 1-(bicyclo[2.2.1]hept-5-en-2-yl)ethan-1-one O-methyl oxime.

The invention also provides a perfumed product comprising:
  a) as fragrance ingredient at least 1-(bicyclo[2.2.1]hept-5-en-2-yl)ethan-1-one O-methyl oxime; and
  b) a consumer product base.

In a further embodiment it is provided a perfumed product comprising:
  a) as fragrance ingredient at least 1-(bicyclo[2.2.1]hept-5-en-2-yl)ethan-1-one O-methyl oxime;
  b) at least one further fragrance ingredient; and
  c) a consumer product base.

As used herein, 'consumer product base' means a composition for use as a consumer product to fulfil specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, eucalyptus oil, lavender oil, and the like. This list of products is given by way of illustration, and is not to be regarded as being in any way limiting.

The invention is now further described with reference to the following non-limiting examples. These examples are for the purpose of illustration only, and it is understood that variations and modifications can be made by one skilled in the art.

All products were purified after work-up by fractional distillation. $^1$H and $^{13}$C NMR spectra were measured in CDCl$_3$. $^1$H NMR spetra in CDCl$_3$ were referenced to the residual hydrogen signal of the deuterated solvent ($^1$H 7.26 ppm, $^{13}$C 77.0 ppm) and are reported as follows: chemical shifts (6 ppm), coupling constants J in Hz. GC-MS analyses were run on a MSD5975 mass spectrometer and are reported as m/z list (relative intensity). Electron ionization (EI) was run at 70 eV. Odor description refers to the odor of the isomeric mixture of the compounds unless otherwise indicated.

EXAMPLE 1: 1-(BICYCLO[2.2.1]HEPT-5-EN-2-YL)ETHAN-1-ONE O-METHYL OXIME

To a solution of O-methylhydroxylamine hydrochloride (19.3 g, 231 mmol, 1.5 equiv), sodium acetate (17.7 g, 216 mmol, 1.4 equiv) in water (54 mL) was added at room temperature a solution of 1-(bicyclo[2.2.1]hept-5-en-2-yl)ethanone (21.0 g, 154 mmol, 1.0 equiv) in MeOH (54 mL) within 2 minutes. The turbid reaction mixture was heated to 65° C. for 6 hours. Since the starting material was fully consumed according to GC analysis, the reaction mixture was diluted with water (250 mL) and MTBE (300 mL). The organic layer was washed with water (1×), sat. NaHCO$_3$ (1×) and brine (2×). The combined aqueous layers were washed once with MTBE. The combined organic extracts were dried over M$_g$SO4, filtered and concentrated under reduced pressure. The crude (26.4 g) was distilled over a 5 cm Vigreux column under reduced pressure (0.07 mbar) to give 1-(bicyclo[2.2.1]hept-5-en-2-yl)ethan-1-one O-methyl oxime (23.0 g, 90% chemical yield) as a colorless oil. This quality was distilled again over a 10 cm Vigreux column at 0.07 mbar to afford 1-(bicyclo[2.2.1]hept-5-en-2-yl)ethan-1-one O-methyl oxime (19.2 g, 75% olfactive yield, mixture of isomers 83:13:4) as a colorless oil (bp 45° C. (0.07 mbar)).

Odor description: green, fruity, anisic banana character. When used at higher concentration the green note becomes more green, fatty violet/watery curcumber.

$^1$H NMR (400 MHz, CDCl$_3$, major isomer 90%): δ 6.13 (dd, J=5.7, 3.1 Hz, 1H), 5.85 (dd, J=5.6, 2.9 Hz, 1H), 3.77 (s, 3H), 3.09-3.04 (m, 1H), 2.88-2.77 (m, 2H), 1.82-1.73 (m, 1H), 1.74 (d, J=0.5 Hz, 3H), 1.45-1.36 (m, 2H), 1.31-1.26 (m, 1H) ppm. $^{13}$C NMR (101 MHz, CDCl$_3$, major isomer): δ 158.8, 136.9, 132.0, 61.0, 49.4, 46.0, 44.3, 42.4, 27.7, 14.0 ppm. Characteristic signals for second isomer (7%): $^1$H NMR (400 MHz, CDCl$_3$): δ 6.17 (dd, J=5.7, 3.1 Hz, 1H), 5.93 (dd, J=5.7, 2.9 Hz, 1H), 3.820 (s, 3H), 3.49-3.41 (m, 1H), 3.24-3.19 (m, 1H) ppm. Characteristic signals for third isomer (3%): $^1$H NMR (400 MHz, CDCl$_3$): δ 6.15-6.08 (m, 2H), 3.815 (s, 3H) ppm. GC-MS (EI) m/z (%, major isomer: t$_R$=5.30 min, 90%): 165 (14, [M]$^{+\bullet}$), 134 (21), 100 (47), 91 (30), 77 (20), 68 (21), 66 (100), 65 (22), 58 (33), 42 (37), 39 (29); GC-MS (EI) m/z (%, second isomer: t$_R$=5.42 min, 7%): 165 (4, [M]$^{+\bullet}$), 100 (78), 99 (12), 91 (16), 68 (23), 66 (100), 65 (15), 58 (28), 42 (23), 39 (22), 27 (11); GC-MS (EI) m/z (%, third isomer: t$_R$=5.21 min, 3%): 165 (4, [M]$^{+\bullet}$), 134 (49), 100 (94), 99 (17), 91 (23), 68 (22), 66 (100), 65 (22), 58 (34), 42 (39), 39 (29). IR (neat, v/cm$^{-1}$): 2968m, 2939m, 2897w, 2870w, 1464w, 1439w, 1366m, 1337m, 1275w, 1239w, 1180w, 1134w, 1049s, 906m, 866s, 833m, 818m, 7563, 722s, 639m.

EXAMPLE 2: 1-(BICYCLO[2.2.1]HEPT-5-EN-2-YL)ETHAN-1-ONE O-METHYL OXIME-ENANTIOENRICHED

An enantioenriched quality of 1-(bicyclo[2.2.1]hept-5-en-2-yl)ethan-1-one O-methyl oxime can be made from enantioenriched 1-(bicyclo[2.2.1]hept-5-en-2-yl)ethanone (known in the literature, e.g. Shanker, R. et al., *J. Org. Chem.* 2008, 73, 212) using the same procedure as reported in Example 1. Such a quality would consist of a blend out of 8 theroretical stereoisomers (endo/exo, E/Z and enantiomers). Those include: (E)-1-((1R,2S,4R)-bicyclo[2.2.1]hept-5-en-2-yl)ethan-1-one O-methyl oxime, (E)-1-((1S,2R,4S)-bicyclo[2.2.1]hept-5-en-2-yl)ethan-1-one O-methyl oxime, (E)-1-((1R,2R,4R)-bicyclo[2.2.1]hept-5-en-2-yl)ethan-1-one O-methyl oxime, (E)-1-((1S,2S,4S)-bicyclo[2.2.1]hept-5-en-2-yl)ethan-1-one O-methyl oxime, (Z)-1-((1R,2S,4R)-bicyclo[2.2.1]hept-5-en-2-yl)ethan-1-one O-methyl oxime, (Z)-1-((1S,2R,4S)-bicyclo[2.2.1]hept-5-en-2-yl)ethan-1-one O-methyl oxime, (Z)-1-((1R,2R,4R)-bicyclo[2.2.1]hept-5-en-2-yl)ethan-1-one O-methyl oxime, (Z)-1-((1S,2S,4S)-bicyclo[2.2.1]hept-5-en-2-yl)ethan-1-one O-methyl oxime.

EXAMPLE 3: FRAGRANCE ACCORD

| Compound/Ingredient | parts by weight 1/1000 |
|---|---|
| BENZALDEHYDE | 1 |
| BENZYL SALICYLATE | 200 |
| CASSYRANE (2-TERT-BUTYL-5-METHYL-2-PROPYL-2,5-DIHYDROFURAN) | 1 |
| β - DAMASCONE | 10 |
| γ-DECALACTONE | 200 |
| GALAXOLIDE (1,3,4,6,7,8-HEXAHYDRO-4,6,6,7,8,8-HEXAMETHYLINDENO(5,6-C)PYRAN) | 100 |
| HEXENOL-3-CIS | 20 |
| LINALOOL | 200 |
| MANZANATE (ETHYL 2-METHYLPENTANOATE) | 10 |
| DIPROPYLENE GLYCOL (DPG) | 258 |
| Total: | 1000 |

The figurative peach, green, juicy and natural fragrance accord above is intended for application in shower gel, e.g. @ 1 wt %.

By replacing 1 part of DPG with 1-(Bicyclo[2.2.1]hept-5-en-2-yl)ethan-1-one O-methyl oxime of Example 1, the performance of the accord is significantly increased.

The fragrance accord above comprising 1 part of 1-(Bicyclo[2.2.1]hept-5-en-2-yl)ethan-1-one O-methyl oxime when used @ 1 wt % in a shower gel, the performance and the diffusion is significantly increased compared to the fragrance accord without 1-(Bicyclo[2.2.1]hept-5-en-2-yl)ethan-1-one O-methyl oxime.

EXAMPLE 4: "BLOOM" PERFORMANCE IN SHAMPOO

To a vessel containing 101 warm water (about 30° C. to 32° C.), enclosed in a non-ventilated standard testing booth, 4 ml of a shampoo comprising 0.2% 1-(bicyclo[2.2.1]hept-5-en-2-yl)ethan-1-one O-methyl oxime from Example 1 was added without mixing. The vessel was located 1.3 meter apart from the door of the booth. After 20 minutes a small window, which is located in the door of the testing booth was opened and the "bloom" performance was assessed by a panel of trained perfumers. The panelists have been asked to assess the "bloom" intensity on a intensity scale from 0 to 5 (0: not perceivable 1: very weak 2: weak 3: medium 4: strong 5: very strong), resulting in a "bloom" intensity of 3.7.

The invention claimed is:

1. A perfumed product comprising:
   a) 1-(bicyclo[2.2.1]hept-5-en-2-yl) ethan-1-one O-methyl oxime; and
   b) a consumer product base selected from the group consisting of household products, laundry products, body care products, cosmetic products and air care products.

2. The perfumed product of claim 1, wherein the 1-(bicyclo[2.2.1]hept-5-en-2-yl) ethan-1-one O-methyl oxime exhibits green fruity anisic banana olfactory properties.

3. A method of improving, enhancing, or modifying the consumer product base of claim 1, said method comprising the step of:
   incorporating 1-(bicyclo[2.2.1]hept-5-en-2-yl) ethan-1-one O-methyl oxime into said consumer product base.

4. A fragrance composition comprising:
   a) 1-(bicyclo[2.2.1]hept-5-en-2-yl) ethan-1-one O-methyl oxime; and
   b) at least one other known fragrance ingredient selected from the group consisting of essential oils and extracts, alcohols, aldehydes, ketones, ethers, acetals, esters, lactones, macrocycles, and heterocycles.

5. The perfumed product of claim 1, which is a fabric softener.

6. The perfumed product of claim 1, which is a detergent product.

7. The perfumed product of claim 6, which is a powdered detergent product.

8. The perfumed product of claim 1, which is a personal care product.

9. An entrapped perfume comprising:
   a) 1-(bicyclo[2.2.1]hept-5-en-2-yl) ethan-1-one O-methyl oxime; and
   b) an entrapment material selected from the group consisting of polymers, capsules, microcapsules and nanocapsules, liposomes, film formers, absorbents, cyclic oligosaccharides and mixtures thereof.

10. The method of claim 3, wherein the enhancement is the provision of an olfactory bloom emanating from the consumer base having comprised within the 1-(bicyclo[2.2.1]hept-5-en-2-yl) ethan-1-one O-methyl oxime.

11. A fragrance composition comprising:
    a) 1-(bicyclo[2.2.1]hept-5-en-2-yl) ethan-1-one O-methyl oxime; and
    b) a base material.

12. A fine perfumery product comprising:
    a) between 0.1 and 30 weight percent of 1-(bicyclo[2.2.1]hept-5-en-2-yl) ethan-1-one O-methyl oxime; and
    b) the consumer product base of claim 1.

* * * * *